United States Patent
Grubis et al.

(10) Patent No.: US 10,354,512 B2
(45) Date of Patent: Jul. 16, 2019

(54) PERIPHERAL ALARM DEVICES FOR GENERATING ALARMS AND MONITORING SYSTEMS INCLUDING ALARM DEVICES

(71) Applicant: General Electric Company, Schenectady, NY (US)

(72) Inventors: Matthew George Grubis, New Berlin, WI (US); Madeline Jay Arpin, Bloomington, MN (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 15/358,565

(22) Filed: Nov. 22, 2016

(65) Prior Publication Data

US 2018/0144600 A1 May 24, 2018

(51) Int. Cl.
*G08B 21/04* (2006.01)
*A61B 5/00* (2006.01)
*G16H 40/63* (2018.01)
*G16H 40/67* (2018.01)
*A61B 5/0205* (2006.01)

(52) U.S. Cl.
CPC ........ *G08B 21/0453* (2013.01); *A61B 5/0002* (2013.01); *A61B 5/746* (2013.01); *G16H 40/63* (2018.01); *G16H 40/67* (2018.01); *A61B 5/0024* (2013.01); *A61B 5/0205* (2013.01); *A61B 5/7221* (2013.01); *A61B 5/7405* (2013.01)

(58) Field of Classification Search
None
See application file for complete search history.

(56) References Cited

U.S. PATENT DOCUMENTS

| | | | | |
|---|---|---|---|---|
| 5,083,109 A | * | 1/1992 | McElroy | G08B 29/10 340/384.5 |
| 2009/0051756 A1 | * | 2/2009 | Trachtenberg | H04N 7/142 348/14.08 |
| 2009/0054736 A1 | | 2/2009 | Rantala et al. | |
| 2016/0283681 A1 | * | 9/2016 | Falck | G06F 19/3406 |
| 2016/0364978 A1 | * | 12/2016 | Warren | G08B 29/10 |
| 2017/0199797 A1 | * | 7/2017 | Hresko | G06F 11/3013 |

OTHER PUBLICATIONS

Darbyshire et al.; An Investigation of sound levels on intensive care units with reference to the WHO guidelines; Critical Care; 2013; 8 pages.

* cited by examiner

*Primary Examiner* — Julie B Lieu
(74) *Attorney, Agent, or Firm* — Dean D. Small; The Small Patent Law Group, LLC (57) ABSTRACT

Peripheral alarm device for a patient monitoring system. In an embodiment, the peripheral alarm device includes an audio speaker and an audio detector. The peripheral alarm device also includes a control system that includes circuitry configured to communicate with the audio detector and a medical software program executed by a host computing system. The audio speaker is configured to generate an audible alarm in response to alarm instructions from the host computing system. The audio detector is configured to communicate a detection signal to the control system. The control system is configured to analyze the detection signal to verify whether the audible alarm was properly generated and communicate a control signal to the host computing system. The peripheral alarm device may include a light indicator and a light detector instead of the audio speaker and the audio detector or in addition to the audio speaker and the audio detector.

20 Claims, 3 Drawing Sheets

PERIPHERAL ALARM DEVICES FOR GENERATING ALARMS AND MONITORING SYSTEMS INCLUDING ALARM DEVICES

BACKGROUND

The subject matter herein relates generally to alarm units and medical systems having the same that are configured to generate an alarm when designated events occur.

Patient monitoring systems are configured to receive physiological signals from a patient, analyze the physiological signals, and communicate information to a healthcare provider so that the healthcare provider may assess the health status of a patient. The physiological signals may include signals that are indicative of, for example, a heart rate, blood pressure, or peripheral oxygen saturation (SpO2). Monitoring systems may include a plurality of acquisition devices that detect the physiological signals and an operator display that presents the information to the healthcare provider. The monitoring systems also include one or more alarms that are configured to alert the healthcare providers to certain events.

Known monitoring systems may determine when a health-related event has occurred and provide an alarm (e.g., audible alarm, flashing light or other visual alarm, tactile movement, etc.) that notifies the healthcare provider of the health-related event. The monitoring system may be located within the same room as the patient or may include components located at a remote site or communicate with the remote site, such as a nurse's station on the same floor as the patient's room or in the same building).

Regardless of the location of the monitoring system, the monitoring system typically includes components that are specially designed for the particular application of the monitoring system. For example, a monitoring system may include a host computing system having specific hardware and pre-installed software that is designed for monitoring cardiovascular parameters, such as blood pressure, heart rate, SpO2, and electrocardiogram (ECG) data. The monitoring system may include a designated user display that shows only a few different screens for displaying the cardiovascular parameters. The monitoring system may also have a dedicated speaker that generates only a few different sounds. While such monitoring systems are effective for carrying out their objectives, the monitoring systems can be expensive and the components are typically not re-configurable or re-usable by the end user for other applications.

BRIEF DESCRIPTION

In an embodiment, a peripheral alarm device for a patient monitoring system is provided. The peripheral alarm device includes a device housing that is discrete with respect to a host computing system of the patient monitoring system. The peripheral alarm device also includes an audio speaker held by the device housing and configured to generate an audible alarm. The peripheral alarm device also includes an audio detector held by the device housing and positioned to detect the audible alarm generated by the alarm device. The peripheral alarm device also includes a control system disposed within the device housing. The control system includes circuitry that is configured to communicate with the audio detector and a medical software program executed by the host computing system for monitoring a patient. The audio speaker is configured to generate the audible alarm in response to alarm instructions from the host computing system. The audio detector is configured to communicate a detection signal to the control system upon detecting the audible alarm. The control system is configured to analyze the detection signal to verify whether the audible alarm was properly generated and communicate a control signal to the host computing system about whether the audible alarm was properly generated.

In some aspects, the audio detector is disposed within an interior of the device housing and has a fixed position relative to the audio speaker.

In some aspects, the circuitry of the control system includes a memory having a set of predetermined alarms stored thereon. The control system is configured to receive the alarm instructions from the host computing system and control the audio speaker to generate the audible alarm. The audible alarm is selected from the set of predetermined alarms based on the alarm instructions.

In some aspects, the control system is configured to analyze the detection signal to determine whether the audible alarm matches at least one of a designated frequency or a designated amplitude.

In some aspects, the alarm instructions are first alarm instructions and the detection signal is a first detection signal. The control system is configured to receive second alarm instructions from the host computing system while the audible alarm is generated by the audio speaker based on the first alarm instructions. The audio detector is configured to communicate a second detection signal to the control system while the audible alarm is generated by the audio speaker based on the first alarm instructions. The control system is configured to analyze the second detection signal to verify that the audible alarm was proper after receiving the second alarm instructions.

In some aspects, the peripheral alarm device is configured to prevent other software on the host computing system from generating sound through the peripheral alarm device.

In some aspects, the peripheral alarm device also includes a pluggable connector that is configured to engage a port of the host computing system. The pluggable connector is configured to communicate a data packet to the host computing system in response to being plugged into the port. The data packet is configured to prevent other software on the host computing system from generating sound through the peripheral alarm device.

Optionally, the data packet at least one of (a) identifies the peripheral alarm device as a generic peripheral device; (b) identifies the peripheral alarm device as other than an audio-capable device; (c) causes the peripheral alarm device to be under the exclusive control of the medical software program; or (d) authenticates or verifies with the medical software program that the peripheral alarm device is an assigned peripheral alarm device.

In some aspects, the control system is configured to communicate with the medical software program to confirm the medical software program is operating properly. The control system initiates corrective action when the medical software program is operating improperly.

In some aspects, the peripheral alarm device is configured to generate a power-loss alarm when the peripheral alarm device has stopped receiving power.

In some aspects, the peripheral alarm device also includes a light indicator and a light detector. The light indicator is configured to generate a visual alarm in response to corresponding alarm instructions from the host computing system. The light detector is configured to communicate a corresponding detection signal to the control system upon detecting the visual alarm. The control system is configured to analyze the corresponding detection signal to verify whether the visual alarm was properly generated and communicate a corresponding control signal to the host computing system about whether the visual alarm was properly generated.

In an embodiment, a patient monitoring system is provided that includes a host computing system configured to execute a medical software program for monitoring a patient. The medical software program is configured to receive physiological signals from a patient and analyze the physiological signals. The patient monitoring system also includes an alarm device having an audio speaker configured to generate an audible alarm and an audio detector positioned to detect the audible alarm generated by the alarm device. The alarm device also includes a control system having circuitry that is configured to communicate with a medical software program executed by the host computing system for monitoring the patient. The audio speaker is configured to generate the audible alarm in response to alarm instructions from the host computing system. The audio detector is configured to detect the audible alarm and communicate a detection signal to at least one of the control system or the host computing system. The detection signal is analyzed to verify whether the audible alarm was properly generated. For example, the detection signal may be analyzed by the control system or by the medical software program on the host computing system.

In some aspects, the alarm device is a peripheral alarm device having a device housing that is discrete with respect to the computing system. The device housing holds the audio speaker and the audio detector.

In some aspects, the peripheral alarm device is configured to prevent other software on the host computing system from generating sound through the peripheral alarm device.

In some aspects, the control system is configured to communicate with the medical software program to confirm the medical software program is operating properly. The control system initiates corrective action when the medical software program is operating improperly.

In some aspects, the host computing system is configured to execute third-party software stored in the host computing system.

In some aspects, the host computing system includes other audio speakers communicatively coupled to the computing system. The other audio speakers may be able to provide sound for other software stored on the host computing system.

In some aspects, the peripheral alarm device is configured to generate a power-loss alarm for a designated period of time when power is not being supplied to the peripheral alarm device.

In an embodiment, a method is provided that includes receiving, at a peripheral alarm device, alarm instructions from a medical software program executed by a host computing system to which the peripheral alarm device is communicatively coupled. The peripheral alarm device has an audio speaker and an audio detector. The method also includes generating, in response to receiving the alarm instructions, an audible alarm by the audio speaker. The method also includes detecting the audible alarm at the audio detector and analyzing the audible alarm to verify whether the audible alarm was properly generated. The method also includes communicating a control signal about whether the audible alarm was properly generated.

In some aspects, generating, in response to receiving the alarm instructions, an audible alarm by the audio speaker includes selecting, based on the alarm instructions, the audible alarm from a set of predetermined alarms stored on the peripheral alarm device.

In an embodiment, a peripheral alarm device for a patient monitoring system is provided. The peripheral alarm device includes a device housing that is discrete with respect to a host computing system of the patient monitoring system. The peripheral alarm device also includes a light indicator held by the device housing and configured to generate a visual alarm. The peripheral alarm device also includes a light detector held by the device housing and positioned to detect the visual alarm generated by the alarm device. The peripheral alarm device also includes a control system disposed within the device housing. The control system includes circuitry that is configured to communicate with the light detector and a medical software program executed by the host computing system for monitoring a patient. The light indicator is configured to generate the visual alarm in response to alarm instructions from the host computing system. The light detector is configured to communicate a detection signal to the control system upon detecting the audible alarm. The control system is configured to analyze the detection signal to verify whether the visual alarm was properly generated and communicate a control signal to the host computing system about whether the visual alarm was properly generated.

In an embodiment, a patient monitoring system is provided that includes a host computing system configured to execute a medical software program for monitoring a patient. The medical software program is configured to receive physiological signals from a patient and analyze the physiological signals. The patient monitoring system also includes an alarm device having a light indicator configured to generate a visual alarm and a light detector positioned to detect the visual alarm generated by the alarm device. The alarm device also includes a control system having circuitry that is configured to communicate with a medical software program executed by the host computing system for monitoring the patient. The light indicator is configured to generate the visual alarm in response to alarm instructions from the host computing system. The light detector is configured to detect the visual alarm and communicate a detection signal to at least one of the control system or the host computing system. The detection signal is analyzed to verify whether the visual alarm was properly generated. For example, the detection signal may be analyzed by the control system or by the medical software program on the host computing system.

In an embodiment, a method is provided that includes receiving, at a peripheral alarm device, alarm instructions from a medical software program executed by a host computing system to which the peripheral alarm device is communicatively coupled. The peripheral alarm device has a light indicator and a light detector. The method also includes generating, in response to receiving the alarm instructions, a visual alarm by the light indicator. The method also includes detecting the visual alarm at the light detector and analyzing the visual alarm to verify whether the visual alarm was properly generated. The method also includes communicating a control signal about whether the visual alarm was properly generated.

In an embodiment, a peripheral alarm device for a patient monitoring system is provided. The peripheral alarm device includes a device housing that is discrete with respect to a host computing system of the patient monitoring system. The peripheral alarm device also includes at least one of a light indicator or an audio speaker held by the device housing and configured to generate an alarm. The peripheral alarm device also includes at least one of a light detector or an audio detector held by the device housing and positioned to detect the alarm by the alarm device. The peripheral alarm device also includes a control system disposed within the device housing. The control system includes circuitry that is configured to communicate with the light detector and/or the audio detector and a medical software program executed by the host computing system for monitoring a patient. The light indicator and/or the audio speaker is configured to generate the alarm in response to alarm instructions from the host computing system. The light detector and/or the audio detector is configured to communicate a detection signal to the control system upon detecting the alarm. The control system is configured to analyze the detection signal to verify whether the alarm was properly generated and communicate a control signal to the host computing system about whether the alarm was properly generated.

DETAILED DESCRIPTION

Embodiments set forth herein are configured to analyze physiological signals to determine whether to issue an audible alarm and/or a visual alarm to a healthcare provider so that the healthcare provider may attend to the patient or make a decision about the patient. At least one technical effect of one or more embodiments includes verifying that the audible alarm and/or visual alarm was properly generated. At least one technical effect of one or more embodiments includes monitoring a medical software program using an alarm device and, upon determining that the medical software program is operating improperly, initiating corrective action by the alarm device. At least one technical effect of one or more embodiments includes permitting the host computing system to use third party software in addition to the medical software program that communicates with the peripheral alarm device. As used herein, the phrase "[A] and/or [B]" means "at least one of A or B."

In some embodiments, the alarm device is a peripheral alarm device. As used herein, the peripheral alarm device includes a device housing that is discrete with respect to the host computing system. For example, the device housing may be configured to be positioned at various desired locations. The peripheral alarm device may include one or more cables and plug connectors that are configured to engage ports of the host computing system. In particular embodiments, the plug connector is a Universal Serial Bus (USB) connector that is configured to be inserted into a USB port of the host computing system. Alternatively or in addition to the above, the peripheral alarm device may be configured to wirelessly communicate with the host computing system. The wireless communication may be in accordance with a wireless technology standard that is configured to exchange data over short distances (e.g., Bluetooth). However, a variety of communication standards may be used. In other embodiments, the alarm device is not a peripheral alarm device and is, instead, integrated with the host computing system.

In some embodiments, the peripheral alarm device is an "intelligent" device in which the peripheral alarm device performs at least some analysis and/or decision-making by circuitry and optional software that is housed within the peripheral alarm device. For example, the peripheral alarm device may include a control system having circuitry that includes at least one of hardwired circuitry and/or one or more processors (e.g., microprocessors). The control system may analyze signals detected by an audio detector (e.g., microphone) to determine whether an audible alarm was properly generated. Alternatively or in addition to signals of an audio detector, the control system may analyze signals detected by a light detector (e.g., photodetector) to determine whether a visual alarm was properly generated. The control system may then communicate with the medical software program to confirm the audible alarm and/or visual alarm was properly or improperly generated.

The intelligent peripheral alarm device may also be configured to communicate with the host computing system such that an assigned or designated medical software program exclusively controls the peripheral alarm device and other software programs are unable to control the peripheral alarm device. It should be understood that more than one medical software program may control the peripheral alarm device. For example, a vendor may provide a suite or bundle of software programs that are capable of controlling the peripheral alarm device. In some cases, the software programs of the same suite or bundle may be configured to communicate with one another and/or may utilize a common device. However, at least one other third party software (e.g., software installed onto the host computing system that is not associated with the vendor or the suite/bundle of software programs) may be unable to recognize and/or communicate with the peripheral alarm device. Accordingly, the peripheral alarm device may be exclusively controlled by an assigned medical software program, which may include only a single assigned medical software program or multiple assigned medical software programs.

In some embodiments, the host computing system is a general purpose computer or a computing system developed by a customer or client. In such instances, the computing system may execute third-party software and/or control other devices (e.g., printer, scanner, camera, microphone, etc.) that were developed independently of the medical software program and/or the peripheral alarm devices. Embodiments may prevent other software on the host computing system from generating sound through the peripheral alarm device. In such instances, the peripheral alarm device may be recognized by the host computing system as a generic peripheral device and/or a device that is other than an audio-capable device and/or a device that is capable of emitting visual electromagnetic radiation. The peripheral alarm device may be under exclusive control of the medical software program.

The control system of the intelligent peripheral alarm device may be configured to communicate with the medical software program to confirm the medical software program is operating properly. If the medical software program is operating improperly, the control system may initiate corrective action. For example, the control system may command the medical software program to re-start. To provide one example of this feature, the control system may include a watchdog timer. If the medical software program fails to communicate with the watchdog timer after a predetermined period of time, the control system may initiate corrective action.

In some embodiments, the intelligent peripheral alarm device may be used to initialize the medical software program. For example, the peripheral alarm device may provide a key to the host computing system when the peripheral alarm device is communicatively coupled to the host computing system that allows the host computing system to use the medical software program.

However, in other embodiments, one or more of the intelligent features described above are performed by the host computing system. For example, the audio detector may communicate detection signals to the host computing system, which analyzes the detection signals to determine the audible alarm was properly generated. Similarly, the light detector may communicate detection signals to the host computing system, which analyzes the detection signals to determine the visual alarm was properly generated.

One or more embodiments may include the host computing system. The host computing system may be, for example, a central computing system that receives and/or analyzes signal data from one or more acquisition devices and/or other patient sources to make a decision on whether an audible alarm should be issued. Alternatively or in addition to this, the central computing system may analyze signal data to make a decision on whether a visual alarm should be issued. It should be understood that the decision to issue an alarm may cause both an audible alarm and a visual alarm to be issued. The computing system may be developed by the customer or client and include software and/or other devices that are not controlled by the medical software program. The audible alarm and/or the visual alarm may be issued upon determining that a designated event has occurred. The designated event may be a health-related event or a system event.

As used herein, a "health-related event" is any event that should be immediately or urgently (e.g., within a few minutes) brought to the attention of a healthcare provider so that the healthcare provider can decide whether and how to act. Such events are more important and urgent than general data collection. For example, although ECGs may be obtained by healthcare providers to assess the general heart health of a patient (e.g., during a follow-up appointment or check-up), ECGs may also be used to detect health-related events, such as a heart attack, that require immediate or urgent consideration or action. Health-related events typically occur in a hospital-like setting in which the patient is being monitored, but embodiments should not be limited to hospital-like settings. The health-related event may be related to a life threatening condition or otherwise potentially harmful condition of the patient.

As used herein, a "system event" is not a health-related event, but an event related to operation of a host computing system, a peripheral alarm device to which the host computing system is communicatively coupled, or an acquisition device to which the host computing system is communicatively coupled. For example, a system event may be identified upon detecting that the peripheral alarm device is disconnected from a power supply. In some embodiments, the peripheral alarm device may be configured to generate a power-loss alarm when the peripheral alarm device has stopped receiving power. The peripheral alarm device may stop receiving power when, for example, the power cable has been disconnected, a battery has been depleted, and/or the host computing (or other power source) has been stopped receiving power or is unable to deliver power. A system event may also be identified upon detecting that an acquisition device is disconnected with the host computing system and/or working improperly. A system event may also be identified upon determining that the medical software program is operating improperly.

Physiological signals includes any signals that may be used to determine (e.g., calculate) a patient parameter. For example, light signals detected by a photodetector in a pulse oximeter may be used to calculate peripheral oxygen saturation (SpO2) data (e.g., the patient parameter). As such, the physiological signals may be signals used to detect vital signs or other parameters measured in a healthcare environment. However, the physiological signals may also be related to a position of the patient, movement of the patient, or images of the patient.

The physiological signals may be acquired by an acquisition device and communicated to the host computing system. Data communicated between the acquisition device and the host computing system is referred to as signal data. The signal data may be the physiological signals unchanged or the signal data may be based on or a function of the physiological signals. For example, the physiological signals may be converted into a signal form typically used in monitoring the patient parameter.

Types of data that may be acquired by embodiments set forth herein include heart rate data, blood pressure data, body temperature data, respiratory rate data, oxygen saturation data (e.g., SpO2 data), image data (e.g., still images, video images, and/or medical images), motion data (e.g., data from an accelerometer), position data (e.g., data from a global positioning system (GPS)), and electrical activity. The data of electrical activity may be, for example, electrocardiographic (ECG) data, cardiotocographic data, electroencephalographic (EEG) data, electromyographic data, or depth of sedation (DOS) data.

The signal data received by the host computing system may include data from acquisition devices (e.g., heart rate monitor, NIBP cuff, pulse oximeter, GPS device, or accelerometer). One or more of the acquisition devices may be capable of issuing an alarm independently. For example, a heart rate monitor may be capable of analyzing the physiological signals and communicating to the host computing system that an audible alarm should be generated and/or that a visual alarm should be issued. In other embodiments, the host computing system may analyze the signal data to determine whether an audible alarm should be generated and/or whether a visual alarm should be generated.

In some embodiments, the host computing system may take into account different data when determining whether to generate an audible alarm and/or a visual alarm. In some embodiments, connectivity between the individual acquisition devices and the master unit is maintained and monitored. If the connection is compromised, the individual acquisition devices may be authorized to issue alarms without permission from the master unit. To this end, the acquisition devices may include an alarm or be communicatively coupled to an alarm. For example, the acquisition device may be capable of generating an audible noise and/or flashing one or more lights.

The medical software program executed by the host computing system and/or software executed by the acquisition devices may use at least one of designated rules, algorithms, or artificial intelligence (AI) to analyze signal data to determine whether the signal data provided is clinically relevant. By way of example, the medical software program may determine that the respiration rate of a patient exceeds a defined threshold. Upon determining that a health-related event has occurred, the host computing system may issue alarm instructions to the peripheral alarm device. The alarm instructions may include the audible alarm to be provided and/or the visual alarm to be provided. For example, the alarm instructions may include a sound file (e.g., file in a designated audio format, such as MP3 or wave audio file format (WAV)) that is to be generated by the peripheral alarm device. Alternatively, the alarm instructions may include data for identifying which sound file, among a set of sound files stored on the peripheral alarm device, should be generated by the peripheral alarm device. As another example, the alarm instructions may include a file that instructs the control system to cause the light indicator to emit visual light at a designated pattern. Alternatively, the alarm instructions may include data for identifying which file, among a set of files stored on the peripheral alarm device, should be generated by the peripheral alarm device.

In some embodiments, the patient monitoring system may be implemented in a tiered structure. For example, a local aggregation point of individual acquisition devices may exist in a patient room. Each of the acquisition devices may be managed by a master unit operating within the patient room. Alternatively, each of the acquisition devices may be managed by the host computing system operating remotely (e.g., on the same level in a hospital or at another location entirely).

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., modules, processors, or memories) may be implemented in a single piece of hardware (e.g., a general purpose signal processor or random access memory, hard disk, or the like). Similarly, programs may be standalone programs, may be incorporated as subroutines in an operating system, may be functions in an installed software package, may be a software surface package that is run from a computer server remotely, and the like. It should be understood that the various embodiments are not limited to the arrangements and instrumentality shown in the drawings.

Figure 1:
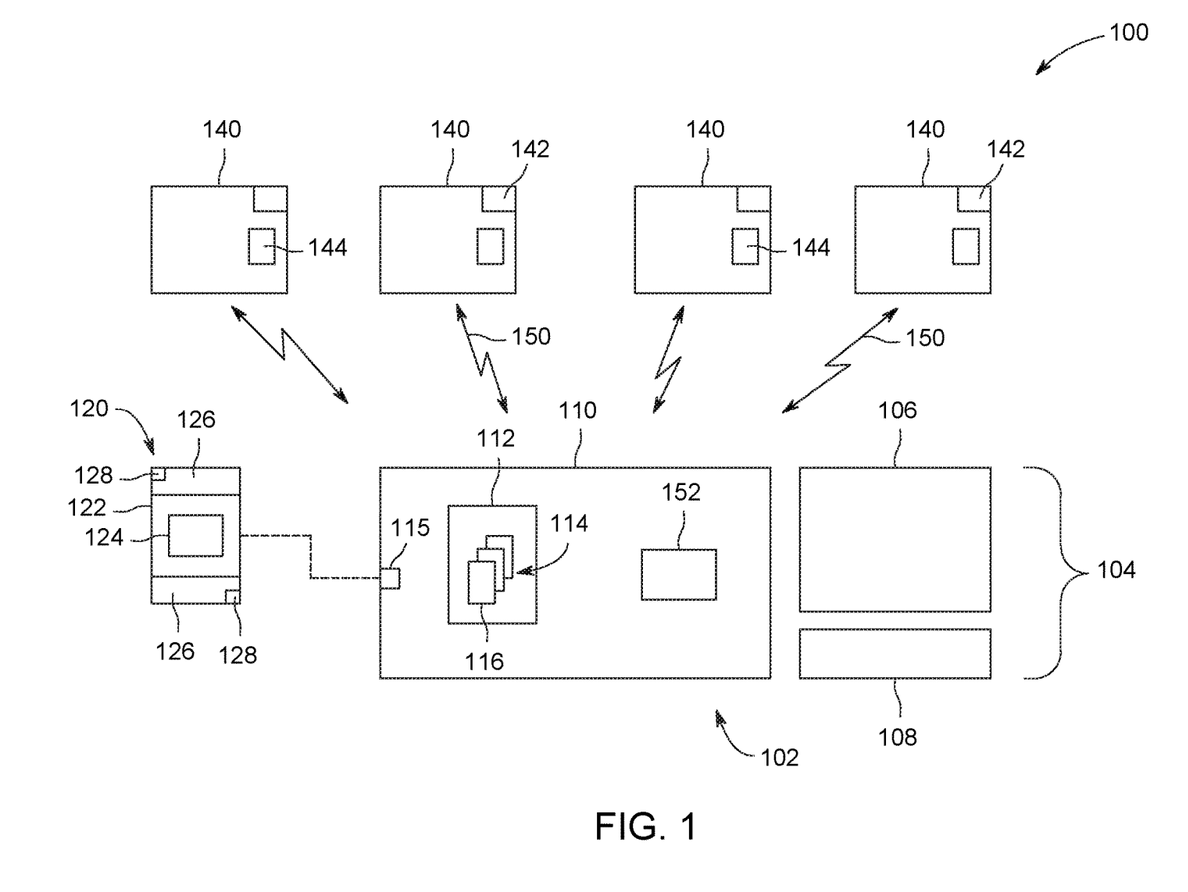
FIG. 1 is a block diagram of a patient monitoring system formed in accordance with an embodiment that is configured to monitor one or more patients.

FIG. 1 is a block diagram of a patient monitoring system 100 (hereinafter "monitoring system") that is configured to monitor a patient. The patient monitoring system 100 includes a host computing system 102 and a plurality of acquisition devices 140 that are communicatively coupled to the host computing system 102. In alternative embodiments, the patient monitoring system 100 may include only one acquisition device 140. The patient monitoring system 100 also includes a user interface 104 that is communicatively coupled to the host computing system 102. The user interface 104 may include instruments (e.g., user display), hardware, and software (or a combination thereof) that permit the system 100 to display information to the user and, in some embodiments, permit the user to provide user inputs or selections. The user may be a healthcare provider, such as a doctor, nurse, or other suitably qualified individual. The user interface 104 may include an operator display 106 (e.g., monitor, screen, touchscreen, and the like) and an input device 108 (e.g., keyboard, computer mouse, tracking button, touchscreen, and the like) that is capable of receiving and communicating user inputs to the host computing system 102. In some embodiments, a device constituting the input device 108 may also be the device constituting the operator display 106. For example, the operator display 106 may be a touch-sensitive screen. The user interface 104 may also be configured to query or prompt the user of the system 100 for designated information.

The host computing system 102 may be integrated into one component (e.g., a laptop computer) or may be several components that may or may not be located near each other. The host computing system 102 includes a base unit 110 that includes hardware of the host computing system. For example, the base unit 110 may include a communication port 115, a processor 114, and memory 116. The memory 116 may include software programs having instructions that are to be executed by the processor 114. The host computing system 102 is configured to execute operations as set forth herein. It is noted that the computing system 102 may not necessarily be limited to a single processor or a single hard-wired device. For example, the computing system 102 may include a single processor (e.g., having one or more cores), multiple discrete processors, one or more application specific integrated circuits (ASICs), and/or one or more field programmable gate arrays (FPGAs). In some embodiments, the computing system 102 includes off-the-shelf components that are appropriately programmed or instructed to perform operations.

Also shown, the patient monitoring system 100 includes an alarm device 120. In some embodiments, the alarm device 120 is a peripheral alarm device having a discrete device housing 122. In other embodiments, however, the alarm device 120 may be integrated with the host computing system 102, such as integrated with the base unit 110 or the user interface 104. Hereinafter, the alarm device 120 will be referred to as the peripheral alarm device 120, but it should be understood that the features of the peripheral alarm device 120 may also be features of an alarm device that is integrated with the host computing system 102. In particular embodiments, the peripheral alarm device 120 may be characterized as a universal serial bus (USB) device, but may not register as a USB audio device with the host computing system 102. Instead, the peripheral alarm device 120 may appear another device, such as a human interface device (HID) or a universal asynchronous receiver/transmitter (UART) device. In particular embodiments, the power source may be provided through the host computing system and the communication port 115. For example, the peripheral alarm device 120 may be powered by USB 2.0 and greater ports.

As shown, the peripheral alarm device 120 includes a control system 124, a plurality of audio speakers 126, and a plurality of audio detectors 128 (e.g., microphones). Alternatively or in addition to the audio speakers 126 and the audio detectors 128, the peripheral alarm device 120 may include a plurality of light indicators 176 and a plurality of light detectors 178 (e.g., photodetectors). The light indicator 176 may be a variety of components that are capable of generating visible electromagnetic radiation. The light indicator 176 may include, for example, one or more light-emitting diodes (LED), a light bulb, a light display, and the like. In particular embodiments, the light indicator 176 is one or more light-emitting diodes. In other embodiments, however, the light indicator 176 may be a more complex device. For example, the light indicator 176 may be a small flat panel display (e.g., liquid crystal display (LCD)).

Although the peripheral alarm device 120 is shown as having multiple audio speakers 126, multiple audio detectors 128, multiple light indicators 176, and multiple light detectors 178, the peripheral alarm device 120 may have, in other embodiments, only one audio speaker 126 and/or only one audio detector 128. In other embodiments, the peripheral alarm device 120 may have only one light indicator 176 and/or only one light detector 178. The control system 124 is communicatively coupled to the audio speakers 126, the audio detectors 128, the light indicators 176, and the light detectors 178. Optionally, the peripheral alarm device 120 includes a cable 130 that is configured to couple to the host computing system 102. The cable 130 may have a plug connector 132 (shown in FIG. 2) that engages the communication port 115.

The host computing system 102 may include one or more software programs 114 stored in memory 112 on the host computing system 102. In some embodiments, the memory 112 may include non-volatile memory. For example, the memory may be or include read-only memory (ROM), random-access memory (RAM), electrically erasable programmable read-only memory (EEPROM), flash memory, and the like. In some embodiments, the host computing system 102 may execute a set of instructions that are stored in one or more storage elements (e.g., of the memory 112), in order to process the physiological signals and control operation of the peripheral alarm device 120 and/or the user interface 104. The set of instructions may include various commands that instruct the host computing system 102 as a processing machine to perform specific operations such as the methods and processes described herein. The software programs 114 may be in various forms such as system software or application software. Further, the software may be in the form of a collection of separate programs, a program module within a larger program or a portion of a program module. The software also may include modular programming in the form of object-oriented programming. The software programs may be compiled to run on designated operating systems.

The software programs 114 may include a medical software program 116 that is configured to monitor physiological signals of one or more patients. The medical software program 116 may be configured to communicate with the acquisition devices 140 to determine whether a health-related event has occurred with one of the patients. For example, the medical software program 116 may analyze signal data received from the acquisition devices 140 to determine whether a health-related event has occurred with one of the patients. Alternatively or in addition to the medical software program analyzing the signal data, the acquisitions devices 140 may analyze the signal data and communicate corresponding alarm instructions to the host computing system 102 when a health-related event has occurred. The medical software program 116 may then communicate alarm instructions to the peripheral alarm device 120 for generating an audible alarm and/or a visual alarm.

The other software programs 114 may be third-party software programs (e.g., developed by a different entity than the entity that developed the medical software program 116). In particular embodiments, the third-party software programs are incapable of using the peripheral alarm device 120.

Each of the acquisition devices 140 may include one or more sensors (or transducers) 142 that are configured to detect physiological signals from the patient (not shown). Each of the acquisition devices 140 may also include device circuitry 144 that is configured to, among other things, control operation of the acquisition device 140. Optionally, the device circuitry 144 may determine whether the corresponding physiological signals satisfy a designated condition. In FIG. 1, communication lines 150 (double-headed arrows) exists between the acquisition devices 140 and the host computing system 102. The communication line 150 may be a physical line (e.g., wires or cables) and/or a wireless connection.

The sensors 142 are configured to detect physiological signals, such as from an individual (e.g., a patient). For example, the sensors 142 may be electrodes configured to detect electrical activity within the patient, such as the electrical activity of the brain, heart, or other muscle. Alternatively or in addition to electrical activity, the sensors 142 may be configured to detect other physiological signals, such as a heart rate, body temperature, blood pressure, respiratory rate, intrauterine pressure, SpO2, etc. The physiological signals may be communicated to the device circuitry 144 of the acquisition device 140 and/or the host computing system 102. Optionally, the physiological signals may be communicated directly to the host computing system 102 (e.g., in analog form).

The host computing system 102 may include or be part of a server system, a workstation, a desktop computer, a laptop computer, or a personal device, such as a tablet computer or a smartphone. However, the above are only examples and the host computing system 102 may be other types of systems or devices. In the illustrated embodiment, the host computing system 102 and/or the base unit 110 includes a system controller 152, which may comprise a controller, processor, or other logic-based device. The system controller 152 may include one or more processors configured to execute the stored programmed instructions of the software programs 114.

Figure 2:
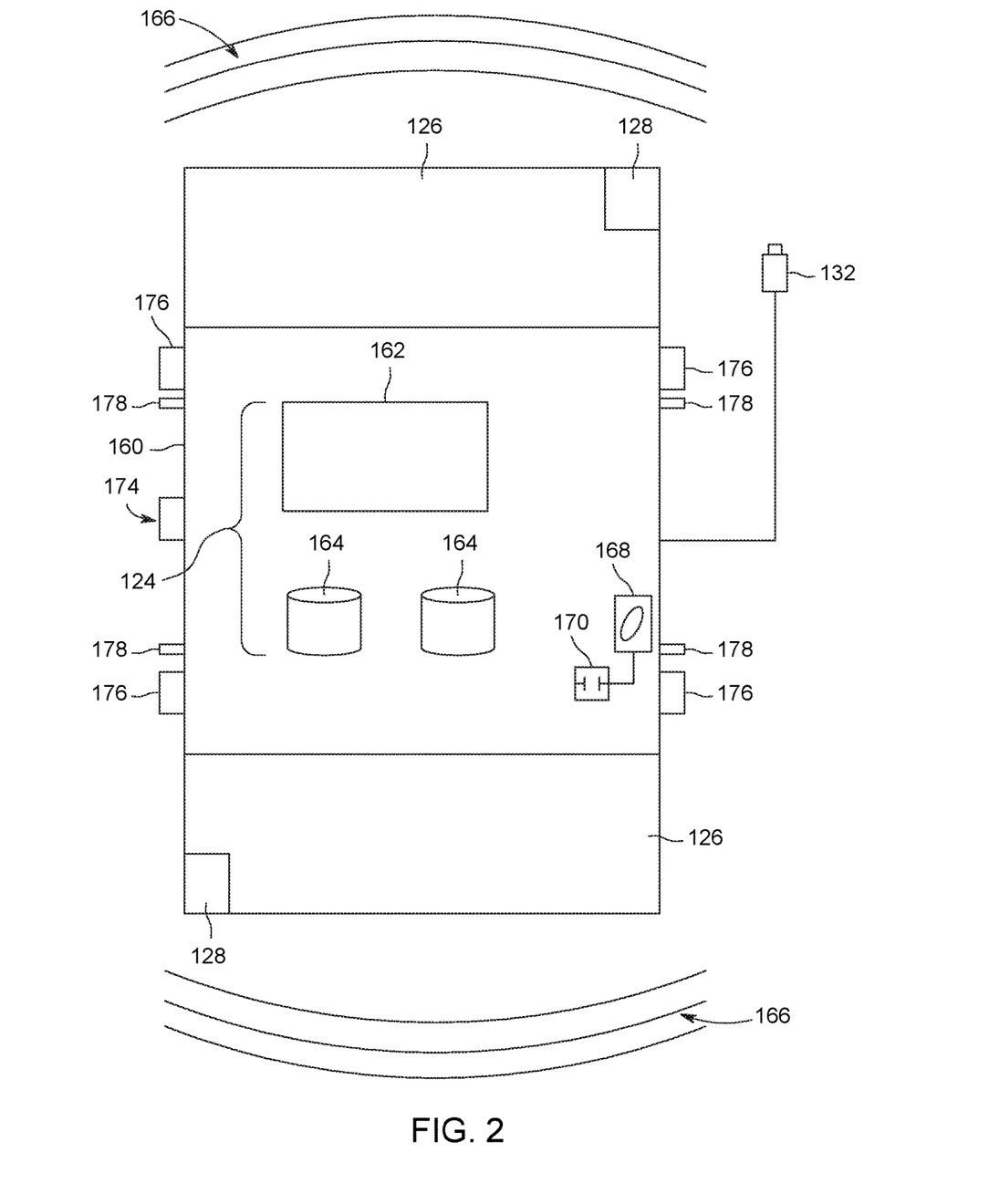
FIG. 2 is a schematic diagram of a peripheral alarm device formed in accordance with an embodiment.

FIG. 2 is a schematic diagram of the peripheral alarm device 120. The peripheral alarm device 120 includes a device housing 160 that is discrete with respect to the host computing system 102 (FIG. 1). For example, the device housing 160 is a standalone housing 160, and the peripheral alarm device 120 may be a self-contained unit that is capable of being moved and positioned as desired. The peripheral alarm device 120 may be less than, for example, twenty (10) kilograms (kg) or less than 8 kg. In more particular embodiments, the peripheral alarm device 120 may be less than 4 kg or less than 2 kg. The peripheral alarm device 120 may be sized and shaped such that the peripheral alarm device 120 may be carried in one hand by an average-sized adult.

In the illustrated embodiment, the audio speakers 126 are held by the device housing 160 and are each configured to generate the audible alarm. As used herein, a component is "held by the device housing" if the component is secured to the device housing such that the component is supported by the device housing and/or if the component is contained within the device housing. The component may be exposed to an exterior of the device housing 160 or may be disposed entirely within the device housing 160.

As shown, the audio speakers 126 face in opposite directions to reduce the likelihood that the audible alarm would not be heard by the healthcare provider. The audio speakers 126 are disposed within the device housing 160. For example, the audio speakers 160 may be within an interior of the peripheral alarm device 120 to reduce the likelihood that a user could inadvertently damage, intentionally alter, or intentionally tamper with the audio speakers 160. Multiple audio speakers 160 may be used for redundancy.

In the illustrated embodiment, the audio detectors 128 are held by the device housing 160 and are positioned to detect the audible alarm generated by the audio speakers 126. Optionally, the audio detectors 128 may be positioned adjacent to the audio speakers 160. For example, the audio detectors 128 may be positioned within 3 centimeters (cm) from the audio speakers 126 or, more specifically, within 2 cm or within 1 cm from the audio speakers 126. The audio detectors 128 may have a fixed position relative to the audio speaker 126 or audio speakers 126.

In the illustrated embodiment, the light indicators 176 are held by the device housing 160 and are each configured to generate the visual alarm. As shown, the light indicators 176 are positioned on opposite sides of the device housing 160. In the illustrated embodiment, the light detectors 178 are held by the device housing 160 and are positioned to detect the visual alarm generated by the light indicators 176. Optionally, the light detectors 178 may be positioned adjacent to the light indicators 176. For example, the light detectors 178 may be positioned within 3 centimeters (cm) from the light indicators 176 or, more specifically, within 2 cm or within 1 cm from the light indicators 176. The light detectors 178 may have a fixed position relative to the light indicators 176. The light indicators 178 may have any position in which it may be possible to detect the visible electromagnetic radiation from the light indicators 176.

The control system 124 is also held by the device housing 160. The control system 124 includes circuitry 162 that is configured to communicate with the audio detectors 128 and the medical software program 116 (FIG. 1) executed by the host computing system 102 (FIG. 1). For example, the circuitry 162 of the control system 124 may include a single processor 162 (e.g., having one or more cores), multiple discrete processors, one or more application specific integrated circuits (ASICs), and/or one or more field programmable gate arrays (FPGAs). The circuitry 162 of the control system 124 may include hardwired circuitry. The circuitry 162 may be configured to communicate with the light detectors 178 and the medical software program 116.

The control system 124 may also include memory 164 (or storage elements 164). In some embodiments, the memory 164 may include stored programmed instructions that, when executed by the circuitry 162 (e.g., by one or more processors), may perform the methods and operations set forth herein. For example, the control system 124 may analyze the audible alarm and/or may communicate with the host computer system 102 (FIG. 1) in a designated manner. The control system 124 may analyze the visual alarm and/or may communicate with the host computer system 102 in a designated manner.

In the following description, embodiments are described in which audio speakers 126 generate an audible alarm that is detected by an audio detector 128. It should be understood that embodiments may include visual indicators 176 that generate a visual alarm that is detected by a light detector 178. Accordingly, the following description with respect to audible alarms may also be applicable with respect to visual alarms. Peripheral alarm devices may be configured to generate an audible alarm and/or a visual alarm. Detection signals from the light detector 178 may be analyzed by the control system.

In particular embodiments, peripheral alarm devices may be configured to generate an audible alarm and a visual alarm that is associated with the audible alarm. For example, the audible alarm may be associated with a designated health-related event. The visual alarm that is generated concurrently (e.g., at an overlapping time and/or the same time) with the audible alarm may be also be associated with a designated health-related event. As such, one or more audible alarms, from a plurality of possible audible alarms, and one or more visual alarms, from a plurality of possible visual alarms, may be generated concurrently. In other embodiments, the audible alarm or the visual alarm may be specific to the health-related event and the other alarm may be generic. For example, the other alarm may be used for any health-related event.

In some embodiments, the audio speakers 126 are configured to generate an audible alarm 166 (indicated by sound waves in FIG. 2) in response to the alarm instructions. In some embodiments, the alarm instructions are communicated from the host computing system 102 to the control system 124. The control system 124 may receive and process the alarm instructions to determine how to proceed. For example, the control system 124 may select the alarm to be generated by the audio speakers 126. The alarm instructions may be communicated directly from the control system 124 to the audio speakers 126. In other embodiments, the alarm instructions are communicated directly from the host computing system 102 to the audio speakers 126.

By way of illustration, the memory 164 may have a set of predetermined alarms stored thereon. The control system 124 may be configured to receive the alarm instructions from the host computing system 102 and control the audio speaker 126 to generate the audible alarm 166 based on the alarm instructions. The audible alarm 166 may be selected from the set of predetermined alarms based on the alarm instructions. More specifically, the memory 164 may include a set of sound files (e.g., MP3 or WAV). The alarm instructions from the host computing system 102 may identify which sound file to use among the set of potential sound files. Each sound file may be used to generate a respective audible alarm. For example, a first sound file may provide an alarm that corresponds to a respiration event, a second sound file may provide an alarm that corresponds to a cardiac event, and a third sound file may provide an alarm that corresponds to an electrical activity event, and so on. In some embodiments, each sound file may include up to five seconds of sound. The sound file may then be repeated by the audio speakers 126 a predetermined number of times and/or until an event occurs (e.g., a healthcare provider acknowledges that the healthcare provider is aware of the health-related event).

Based on the alarm instructions, the control system 124 may identify the sound file to use and communicate the sound file to the audio speakers 126 and/or control the audio speakers 126 to generate the audible alarm 166. The audio detectors 128 may communicate a detection signal to the control system 124 upon detecting the audible alarm. The detection signal may be based on the detected audible alarm 166. For example, the detection signal may be an analog signal of the audible alarm. Alternatively, the detection signal may only be sampled points of the audible alarm 166. The sampled points may provide sufficient information for identifying and/or verifying that the audible alarm 166 was generated by the audio speakers 126. The control system 124 is configured to analyze the detection signal to verify whether the audible alarm 166 was properly generated. The control system 124 may communicate a control signal to the host computing system 102 about whether the audible alarm was properly generated.

In some embodiments, when the control system 124 analyzes the detection signal to verify whether the audible alarm 166 was properly generated, the control system 124 may analyze the detection signal to determine whether the audible alarm 166 matches at least one of a designated frequency or a designated amplitude. In particular embodiments, the control system 124 analyzes the detection signal to determine whether the audible alarm 166 matches a designated frequency and a designated amplitude. However, it should be understood that the control system 124 may perform other types of analyses to confirm that the audible alarm 166 was generated properly.

The peripheral alarm device 120 may be configured to prevent the user from changing the volume and/or turning off the peripheral alarm device. For example, the peripheral alarm device 120 may be devoid of tangible elements (e.g., buttons or knobs) for changing the volume of the audible alarms and/or disconnecting the peripheral alarm device from the power source. The peripheral alarm device may be configured to generate a power-loss alarm for a designated period of time (e.g., five minutes) when the peripheral alarm device has stopped receiving power.

In some embodiments, the peripheral alarm device 120 is configured to generate only one type of audible alarm at a time. In some situations, a second health-related event from the same patient or from a different patient may occur while the audible alarm from a prior first health-related event is being generated. Embodiments may be configured to override the audible alarm from the first health-related event and provide a different audible alarm for the second health-related event.

In some situations, a health-related event may occur a second time before the audible alarm from the first time ceases or stops being sounded. Embodiments may be configured to verify that the audible alarm was properly generated the first time and verify that the audible alarm continues to be properly generated for the subsequent health-related event. In such instances, the audible alarm is not disrupted when the subsequent health-related event is detected. Instead, the audible alarm is provided continuously without interruption.

More specifically, the control system 124 may receive first alarm instructions from the host computing system 102 and generate an audible alarm, as described above, based on the first alarm instructions. The audio detectors 128 are configured to communicate a first detection signal to the control system 124 while the audible alarm is generated by the audio speaker based on the first alarm instructions. The control system 124 may then receive second alarm instructions from the host computing system 102 while the audible alarm based on the first alarm instructions continues to be provided by the audio speakers 126. The second alarm instructions may be for the same type of health-related event for the same patient. The audio detectors 128 are configured to communicate a second detection signal to the control system 124 while the audible alarm is generated by the audio speaker based on the first alarm instructions. The control system 124 is configured to analyze the second detection signals to confirm that the audible alarm 166 was proper after receiving the second alarm instructions.

Optionally, the peripheral alarm device 120 is configured to prevent other software programs 114 on the host computing system 102 from generating sound through the peripheral alarm device 120. For example, the peripheral alarm device 120 may communicate a data packet to the host computing system 102 in response to being communicatively coupled to the host computing system 102. For example, the plug connector 132 may be engaged to the communication port 115 (FIG. 1). The data packet may be configured to prevent other software programs on the host computing system 102 from generating sound through the peripheral alarm device 120. In some embodiments, the data packet at least one of (a) identifies the peripheral alarm device as a generic peripheral device; (b) identifies the peripheral alarm device as other than an audio-capable device; (c) causes the peripheral alarm device to be under the exclusive control of the medical software program; or (d) authenticates or verifies with the medical software program that the peripheral alarm device is an assigned peripheral alarm device. An assigned peripheral alarm device may be an alarm device that is designed to communicate with designated (or assigned) medical software and/or a designated computing system, but not other medical software programs or computing systems. The peripheral alarm device may authenticate or verify that the peripheral alarm device is an assigned peripheral alarm device of the medical software program and/or the computing system by using an authentication process (e.g., a device authentication process). In some embodiments, the peripheral alarm device 120 may appear as a human interface device (HID) or as a universal asynchronous receiver/transmitter (UART) device.

In some embodiments, the data packet is provided directly by the plug connector 132. More specifically, the plug connector 132 may include circuitry that provides the data packet in response to determining that the plug connector 132 has engaged the communication port 115. In other embodiments, the data packet is communicated by the control system 124 through the plug connector 132 or communicated wirelessly by the control system 124.

In particular embodiments, the control system 124 of the peripheral alarm device 120 is configured to communicate with the medical software program 116 to confirm the medical software program 116 is operating properly. The control system 124 may initiate corrective action when the medical software program 166 is operating improperly. For example, the control system 124 may include a watchdog timer. If the medical software program 116 fails to communicate with the watchdog timer after a predetermined period of time, the control system 124 may initiate corrective action. For example, the control system 124 may instruct the medical software program to exit and/or shut down and restart.

Optionally, the peripheral alarm device 120 may have a separate audio device 168 (e.g., a buzzer) that is activated when a designated event has occurred. For example, the audio device 168 may begin generating a noise when the peripheral alarm device 120 is disconnected from a power source. When power to the peripheral alarm device 120 is lost, the audio device 168 is activated and generates a sound (e.g., buzz) for a designated period of time (e.g., at least two minutes). In particular embodiments, the audio device 168 is powered by a supercapacitor 170 when there is no other power source.

In some embodiments, the peripheral alarm device 120 includes one or more visual indicators 174. Different colors and/or blinking frequencies may represent different statuses of the peripheral alarm device 120. For example, if the visual indicator 174 is blinking green, the peripheral alarm device 120 is powered but has not been authenticated with software. If the visual indicator 174 is solid green, the peripheral alarm device 120 is powered and authenticated with the medical software program. If the visual indicator 174 is solid red, the peripheral alarm device 120 may be without a power source. If the visual indicator 174 is blinking red, the peripheral alarm device 120 is powered but an internal error has been detected.

Figure 3:
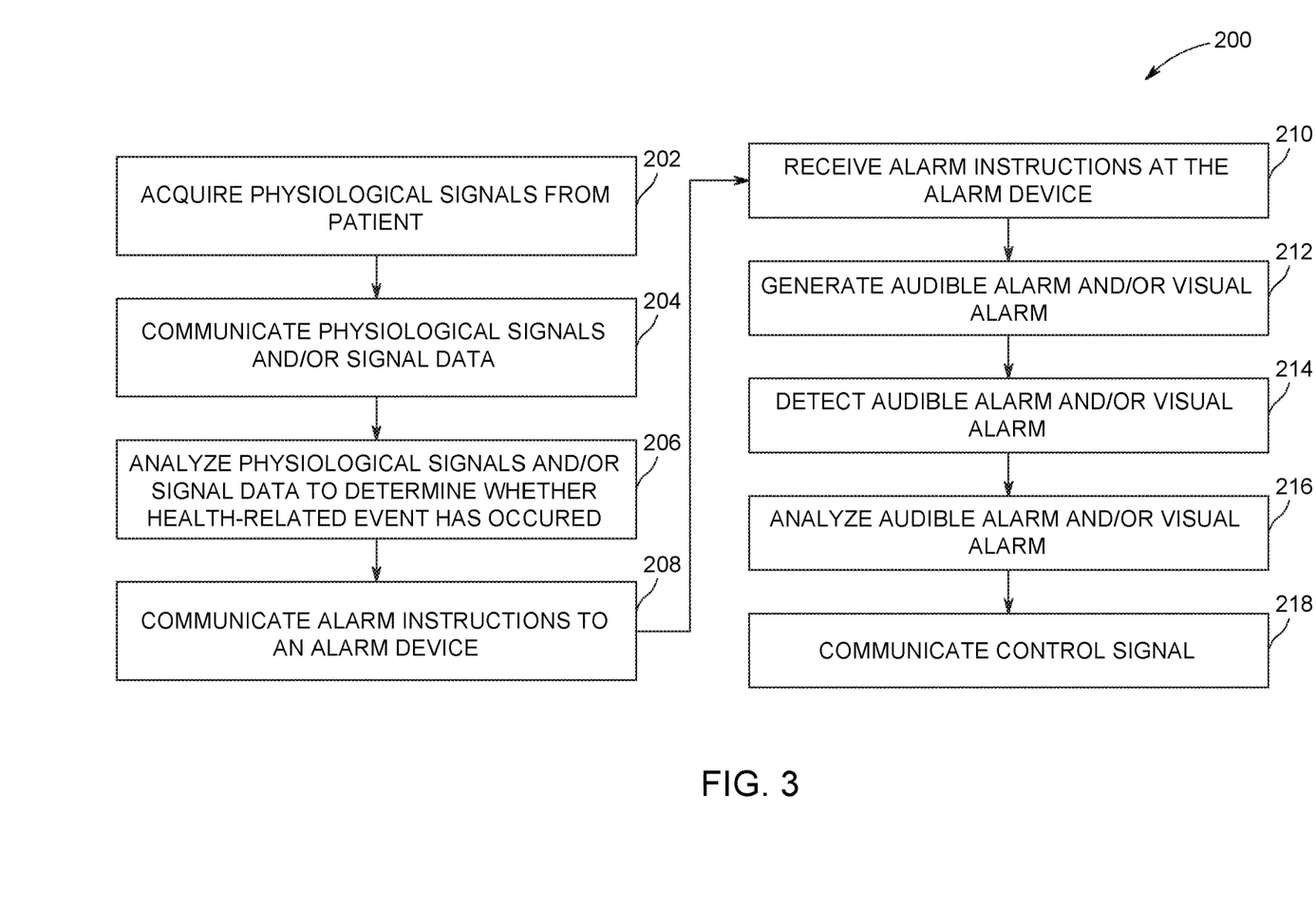
FIG. 3 is a flow chart illustrating a method of monitoring a patient in accordance with an embodiment.

FIG. 3 is a flow chart illustrating a method 200 of monitoring a patient in accordance with an embodiment. The method 200, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

The method 200 includes acquiring, at 202, physiological signals from a patient. The patient may be human or other animal. The physiological signals may be suitable for determining (e.g., calculating) a patient parameter. By way of example, the physiological signals may be signals from a pressure sensor in an automated non-invasive blood pressure device. The signals may be used to calculate blood pressure.

At 204, the physiological signals and/or signal data based on the physiological signals are communicated to the host computing system. In some embodiments, the host computing system analyzes, at 206, the physiological signals and/or signal data to determine whether a health-related event has occurred. In other embodiments, the acquisition device may analyze, at 206, the physiological signals and/or signal data to determine whether a health-related event has occurred and communicate such information to the host computing system. At 208, the host computing system may communicate alarm instructions to an alarm device, such as the peripheral alarm devices described herein. A medical software program running on the host computing system may cause the alarm instructions to be communicated to the peripheral alarm device. In alternative embodiments, the alarm instructions may be communicated directly from an acquisition device.

At 210, the alarm instructions are received at the alarm device. The alarm device may have an audio speaker and an audio detector and/or a light indicator and light detector. Based on the alarm instructions, an audible alarm may be selected from a set of predetermined alarms. The method 200 also includes generating, at 212, in response to receiving the alarm instructions, an audible alarm by the audio speaker and/or a visual alarm by the light indicator. At 214, the audible alarm is detected by the audio detector. The visual alarm may be detector by a light detector. At 216, the alarm (e.g., audible alarm and/or the visual alarm) is analyzed to verify whether the alarm was properly generated. The analyzing may be performed by the peripheral alarm device or, more specifically, by a control system of the peripheral alarm device. Alternatively, the analyzing may be performed by the host computing system. At 218, a control signal about whether the alarm was properly generated is communicated to the host computing system. The control signal may confirm that the alarm was properly generated or may determine that the alarm was improperly generated.

If the audible alarm was improperly generated, the medical software program may display information to the user on the operator display. The information may inform the user that one or more audible alarms were not generated by peripheral alarm device. Similarly, if the visual alarm was improperly generated, the medical software program may display information to the user on the operator display. The information may inform the user that one or more visual alarms were not generated by peripheral alarm device. The user may then inspect the alarm device or replace the alarm device.

As used herein, the terms "computer" or "computing system" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "computing system."

The computer or processor executes a set of instructions that are stored in one or more storage elements, in order to process input data and provide output data in the form of a health chart, among other things. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes described herein. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine. The program is compiled to run on designated operating systems.

As used herein, an element or step recited in the singular and proceeded with the word "a" or "an" should be understood as not excluding plural of said elements or steps, unless such exclusion is explicitly stated. For example, the phrase "a processor" may include a single processor, a multi-core processor, or a plurality of processors. If a plurality of processors are used, the plurality of processors may be found within a single unit (e.g., computer) or may be distributed throughout a system, such as in multiple units. If one processor is used, the claims may recite the processor as "only a single processor."

Furthermore, references to "one embodiment" are not intended to be interpreted as excluding the existence of additional embodiments that also incorporate the recited features. Moreover, unless explicitly stated to the contrary, embodiments that "comprise," "have," or "include" an element or a plurality of elements that have a particular property may also include additional such elements that do not have that particular property. Furthermore, when a feature is described as being based on a factor (e.g., signal data or physiological signals) or being a function of a factor, the term "based on" or "function of" should not be interpreted as the factor being the sole factor or primary factor, but may include the possibility that the element is also based on other factors.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A peripheral alarm device for a patient monitoring system, the peripheral alarm device comprising:
    a device housing that is discrete with respect to a host computing system of the patient monitoring system;
    an audio speaker held by the device housing and configured to generate an audible alarm;
    an audio detector held by the device housing and positioned to detect the audible alarm generated by the alarm device; and
    a control system disposed within the device housing, the control system including circuitry that is configured to communicate with the audio detector and a medical software program executed by the host computing system for monitoring a patient;
    wherein the audio speaker is configured to generate the audible alarm in response to alarm instructions from the host computing system, the audio detector configured to communicate a detection signal to the control system upon detecting the audible alarm, the control system configured to analyze the detection signal to verify whether the audible alarm was properly generated and communicate a control signal to the host computing system about whether the audible alarm was properly generated, wherein the peripheral alarm device is configured to prevent other software on the host computing system from generating sound through the peripheral alarm device.

2. The peripheral alarm device of claim 1, wherein the circuitry of the control system includes a memory having a set of predetermined alarms stored thereon, the control system configured to receive the alarm instructions from the host computing system and control the audio speaker to generate the audible alarm, the audible alarm being selected from the set of predetermined alarms based on the alarm instructions, wherein the control system is configured to analyze the detection signal to determine whether the audible alarm matches at least one of a designated frequency or a designated amplitude.

3. The peripheral alarm device of claim 1, wherein the alarm instructions are first alarm instructions and the detection signal is a first detection signal, the control system configured to receive second alarm instructions from the host computing system while the audible alarm is generated by the audio speaker based on the first alarm instructions, wherein the audio detector is configured to communicate a second detection signal to the control system while the audible alarm is generated by the audio speaker based on the first alarm instructions, the control system configured to analyze the second detection signal to verify that the audible alarm was proper after receiving the second alarm instructions.

4. The peripheral alarm device of claim 1, further comprising a pluggable connector that is configured to engage a port of the host computing system, the pluggable connector configured to communicate a data packet to the host computing system in response to being plugged into the port, the data packet configured to prevent the other software on the host computing system from generating sound through the peripheral alarm device.

5. The peripheral alarm device of claim 4, wherein the data packet at least one of:
    (a) identifies the peripheral alarm device as a generic peripheral device;
    (b) identifies the peripheral alarm device as other than an audio-capable device;
    (c) causes the peripheral alarm device to be under the exclusive control of the medical software program; or
    (d) authenticates or verifies with the medical software program that the peripheral alarm device is an assigned peripheral alarm device.

6. The peripheral alarm device of claim 1, wherein the control system is configured to communicate with the medical software program to confirm the medical software program is operating properly, the control system initiating corrective action when the medical software program is operating improperly.

7. The peripheral alarm device of claim 1, further comprising a light indicator and a light detector, wherein the light indicator is configured to generate a visual alarm in response to corresponding alarm instructions from the host computing system, the light detector configured to communicate a corresponding detection signal to the control system upon detecting the visual alarm, the control system configured to analyze the corresponding detection signal to verify whether the visual alarm was properly generated and communicate a corresponding control signal to the host computing system about whether the visual alarm was properly generated.

8. The peripheral alarm device of claim 1, wherein the peripheral alarm device is configured to communicate a data packet to the host computing system to prevent the other software on the host computing system from generating sound through the peripheral alarm device, wherein the data packet at least one of:
    (a) identifies the peripheral alarm device as a generic peripheral device;
    (b) identifies the peripheral alarm device as other than an audio-capable device;
    (c) causes the peripheral alarm device to be under the exclusive control of the medical software program; or
    (d) authenticates or verifies with the medical software program that the peripheral alarm device is an assigned peripheral alarm device.

9. A peripheral alarm device for a patient monitoring system, the peripheral alarm device comprising:
    a device housing that is discrete with respect to a host computing system of the patient monitoring system;
    an audio speaker held by the device housing and configured to generate an audible alarm;
    an audio detector held by the device housing and positioned to detect the audible alarm generated by the alarm device; and a control system disposed within the device housing, the control system including circuitry that is configured to communicate with the audio detector and a medical software program executed by the host computing system for monitoring a patient;

wherein the audio speaker is configured to generate the audible alarm in response to alarm instructions from the host computing system, the audio detector configured to communicate a detection signal to the control system upon detecting the audible alarm, the control system configured to analyze the detection signal to verify whether the audible alarm was properly generated and communicate a control signal to the host computing system about whether the audible alarm was properly generated, wherein the peripheral alarm device is configured to generate a power-loss alarm when the peripheral alarm device has stopped receiving power.

10. The peripheral alarm device of claim 9, wherein the peripheral alarm device is configured to detect when at least one of a power cable has been disconnected, a battery has been depleted, or a power source to which the peripheral alarm device is coupled is unable to deliver power.

11. The peripheral alarm device of claim 9, further comprising a port that is configured to receive power and communicate with the host computing system.

12. The peripheral alarm device of claim 9, wherein the peripheral alarm device has at least one visual indicator that indicates a power status of the peripheral alarm device and whether the peripheral alarm device has been authenticated.

13. The patient monitoring system of claim 9, wherein the power-loss alarm is generated for a designated period of time when power is not being supplied to the peripheral alarm device.

14. A patient monitoring system comprising:

a host computing system configured to execute a medical software program for monitoring a patient, the medical software program configured to receive physiological signals from a patient and analyze the physiological signals, wherein the host computing system is at least one of a general-purpose desktop computer, laptop computer, tablet computer, or smartphone; and an alarm device including an audio speaker configured to generate an audible alarm and an audio detector positioned to detect the audible alarm generated by the alarm device, the alarm device also including a control system having circuitry that is configured to communicate with the medical software program executed by the host computing system for monitoring the patient, wherein the host computing system has one or more processors that are distinct from the control system and that are configured to execute stored programmed instructions of a third-party software;

wherein the audio speaker is configured to generate the audible alarm in response to alarm instructions from the host computing system, the audio detector configured to detect the audible alarm and communicate a detection signal to at least one of the control system or the host computing system, wherein the detection signal is analyzed to verify whether the audible alarm was properly generated.

15. The patient monitoring system of claim 14, wherein the alarm device is a peripheral alarm device having a device housing that is discrete with respect to the computing system, the device housing holding the audio speaker and the audio detector.

16. The patient monitoring system of claim 15, wherein the peripheral alarm device is configured to prevent other software on the host computing system from generating sound through the peripheral alarm device.

17. The patient monitoring system of claim 15, wherein the control system is configured to communicate with the medical software program to confirm the medical software program is operating properly, the control system initiating corrective action when the medical software program is operating improperly.

18. The patient monitoring system of claim 15, wherein the host computing system is configured to execute third-party software stored in the host computing system.

19. The patient monitoring system of claim 14, wherein the alarm device is configured to prevent other software programs on the host computing system from generating sound through the alarm device.

20. The patient monitoring system of claim 14, further comprising the medical software program stored onto the host computing system, the medical software program being the third-party software.

* * * * *